US00PP18623P2

(12) United States Plant Patent
Hurkman

(10) Patent No.: US PP18,623 P2
(45) Date of Patent: Mar. 18, 2008

(54) ***PETUNIA* PLANT NAMED 'BALSUNDARCO'**

(50) Latin Name: *Petunia×hybrida*
Varietal Denomination: Balsundarco

(75) Inventor: Margaret M. Hurkman, Santa Maria, CA (US)

(73) Assignee: Ball Horticultural Company, West Chicago, IL (US)

( * ) Notice: Subject to any disclaimer, the term of this patent is extended or adjusted under 35 U.S.C. 154(b) by 30 days.

(21) Appl. No.: 11/594,259

(22) Filed: Nov. 8, 2006

(51) Int. Cl.
*A01H 5/00* (2006.01)

(52) U.S. Cl. ..... Plt./356
(58) Field of Classification Search ..... Plt./356
See application file for complete search history.

(56) References Cited

U.S. PATENT DOCUMENTS

PP16,731 P2 * 6/2006 Uchneat ..... Plt./356
PP18,128 P2 * 10/2007 Kerley et al. ..... Plt./356

OTHER PUBLICATIONS

UPOV ROM GTITM Computer Database, GTI Jouve Retrieval Software 2007/02 Citation for 'Balsundarco'.*

* cited by examiner

*Primary Examiner*—Wendy Haas
(74) *Attorney, Agent, or Firm*—Audrey Charles

(57) ABSTRACT

A new and distinct cultivar of *Petunia* plant named 'Balsundarco', characterized by its single type, dark coral-colored flowers, dark green-colored foliage, and moderately vigorous, mounded -trailing growth habit.

1 Drawing Sheet

Latin name of genus and species of plant claimed: *Petunia×hybrida.*
Variety denomination: 'Balsundarco'.

BACKGROUND OF THE INVENTION

The present invention relates to a new and distinct cultivar of *Petunia* plant botanically known as *Petunia×hybrida* and hereinafter referred to by the cultivar name 'Balsundarco'.

The new cultivar originated in a controlled breeding program in Arroyo Grande, Calif. during February 2004. The objective of the breeding program was the development of *Petunia* cultivars with single type flowers, unique flower coloration, and a vigorous, mounded-trailing growth habit.

The new *Petunia* cultivar is the result of cross-pollination. The female (seed) parent of the new cultivar is the proprietary *Petunia×hybrida* breeding selection designated 1694-1, not patented, characterized by its single type, scarlet red-colored flowers, dark green-colored foliage, and well-branched, trailing growth habit. The male (pollen) parent of the new cultivar is the proprietary *Petunia×hybrida* breeding selection designated SA2091-1, not patented, characterized by its single type, medium coral-colored flowers, medium green-colored foliage, and trailing growth habit. The new cultivar was discovered and selected as a single flowering plant within the progeny of the above stated cross-pollination during October 2004 in a controlled environment at Arroyo Grande, Calif.

Asexual reproduction of the new cultivar by terminal stem cuttings since October 2004 at Arroyo Grande, Calif. and West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balsundarco' as a new and distinct cultivar of *Petunia* plant:

1. Single type, dark coral-colored flowers;
2. Dark green-colored foliage; and
3. Moderately vigorous, mounded-trailing growth habit.

Plants of the new cultivar differ from plants of the female parent primarily in flower color and growth habit and from plants of the male parent primarily in flower color, foliage color, and growth habit.

Of the many commercially available *Petunia* cultivars known to the inventor, the most similar in comparison to the new cultivar is Suncatcher™ Coral Prism 'Balsuncora', U.S. Plant Pat. No. 16,731. However, in side by side comparisons, plants of the new cultivar differ from plants of 'Balsuncora' in the following characteristics:

1. Plants of the new cultivar have a petal color different from plants of 'Balsuncora'; and
2. Plants of the new cultivar have a corolla tube color different from plants of 'Balsuncora'.

In addition, plants of the new cultivar are similar in comparison to Suncatcher™ Salmon Vein 'Kersamfan', U.S. Plant Pat. No. 18,128. However, in side by side comparisons, plants of the new cultivar differ from plants of 'Kersamfan' in the following characteristics:

1. Plants of the new cultivar lack venation and have a petal color different from plants of 'Kersamfan'; and
2. Plants of the new cultivar are taller than plants of 'Kersamfan'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Balsundarco'. The plants were grown in 4.5 inch pots for 9 weeks in a greenhouse at West Chicago, Ill.

DETAILED BOTANICAL DESCRIPTION

Figure 1:
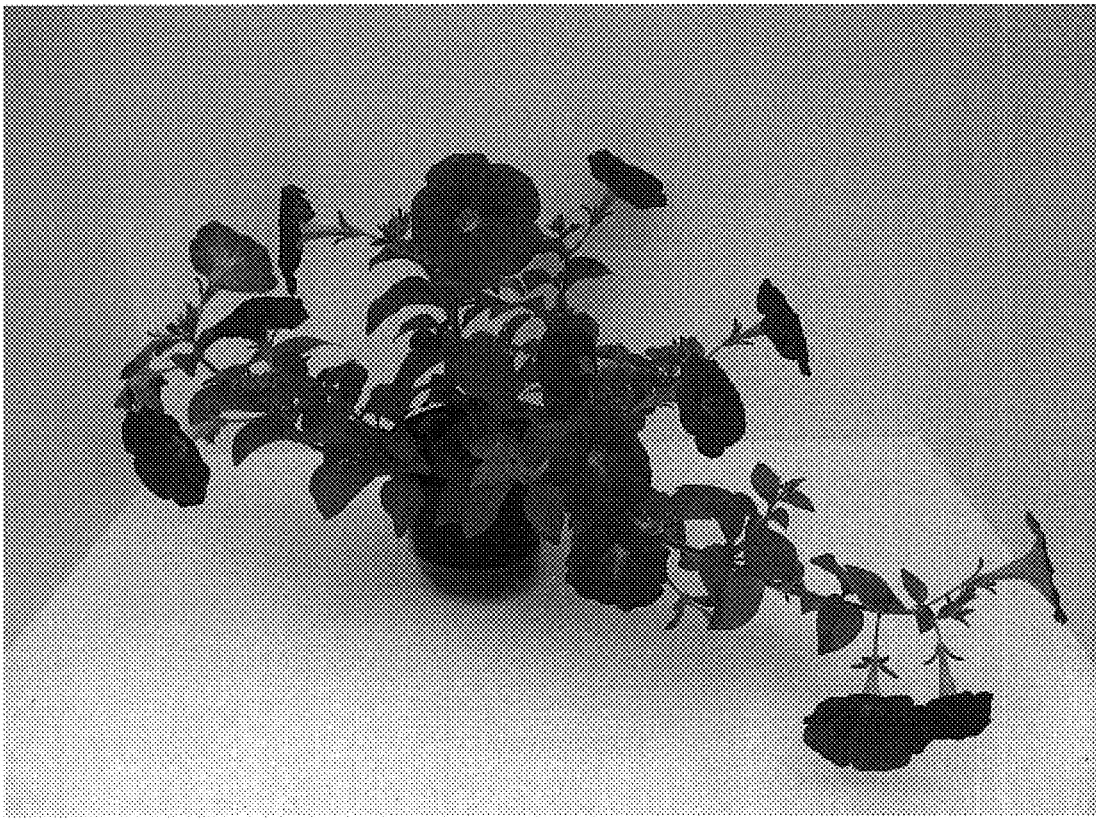
FIG. 1 illustrates a side view of the overall growth and flowering habit of 'Balsundarco'.
Figure 2:
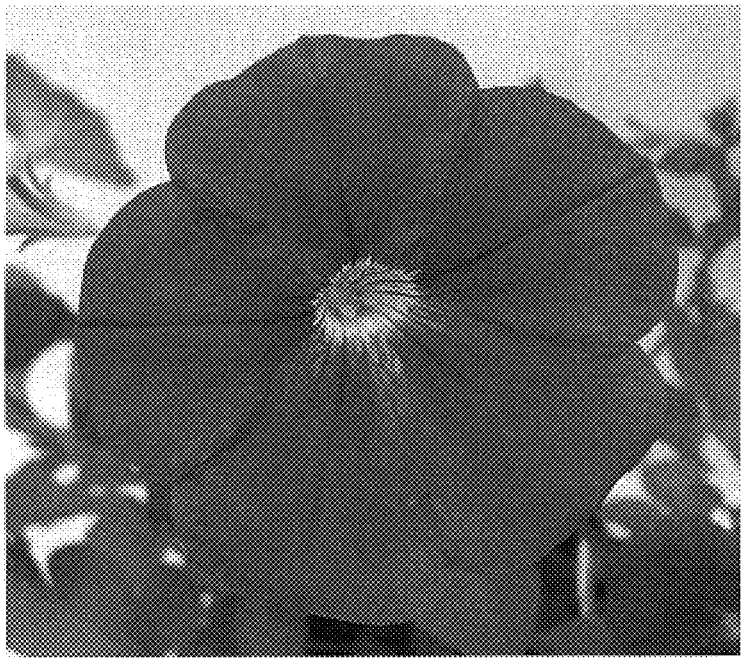
FIG. 2 illustrates a close-up view of an individual flower of 'Balsundarco'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2001 edition, except where general color terms of ordinary significance are used. The color values were determined on Feb. 2, 2006 between 9:00 a.m. and 11:00 a.m. under natural light conditions in West Chicago, Ill.

The following descriptions and measurements describe plants produced from cuttings taken from stock plants and grown in a glass-covered greenhouse under conditions comparable to those used in commercial practice. The plants were grown at West Chicago, Ill. in 4.5 inch pots for 9 weeks utilizing a soilless growth medium. Greenhouse temperatures were maintained at approximately 70° F. to 77° F. (21° C. to 25° C.) during the day and approximately 65° F. to 68° F. (18° C. to 20° C.) during the night. Greenhouse light levels of 2,500 footcandles to 6,000 footcandles were maintained during the day.

Botanical classification: *Petunia×hybrida* cultivar Balsundarco.

Parentage:

*Female parent.*—Proprietary *Petunia×hybrida* breeding selection designated 1694-1, not patented.

*Male parent.*—Proprietary *Petunia×hybrida* breeding selection designated SA2091-1, not patented.

Propagation:

*Type cutting.*—Terminal stem.

*Time to initiate roots.*—Approximately 6 to 9 days.

*Time to produce a rooted cutting.*—Approximately 21 to 28 days.

*Root description.*—Fibrous.

*Rooting habit.*—Freely branching.

Plant description:

*Commercial crop time.*—Approximately 6 to 8 weeks from a rooted cutting.

*Growth habit and general appearance.*—Moderately vigorous, mounded-trailing.

*Size.*—Height from soil level to top of plant plane: Approximately 21.3 cm. Width: Approximately 56.7 cm.

*Branching habit.*—Freely branching. Quantity of main branches per plant: Approximately 5.

*Branch.*—Strength: Strong. Length: Approximately 30.8 cm. Diameter: Approximately 3.8 mm. Length of central internode: Approximately 4.2 cm. Texture: Densely glandular pubescent with a mixture of long and short hairs. Gland color: Colorless: Color of young and mature stems: 144A.

Foliage description:

*General description.*—Quantity of leaves per main branch: Approximately 12. Fragrance: Slight. Form: Simple. Arrangement on flowering stem: Opposite.

*Leaves.*—Aspect: Acute angle to stem. Shape: Ovate. Margin: Entire. Apex: Acute. Base: Attenuate. Venation pattern: Pinnate. Length of mature leaf: Approximately 5.8 cm. Width of mature leaf: Approximately 4.7 cm. Texture of upper and lower surfaces: Densely glandular pubescent with a mixture of long and short hairs. Gland color: Colorless. Color of upper surface of young and mature foliage: 137C with venation of 144B. Color of lower surface of young and mature foliage: 138B with venation of 144B.

*Petiole.*—Length: Approximately 7.5 mm. Width: Approximately 4.0 mm. Texture: Densely glandular pubescent with a mixture of long and short hairs. Gland color: Colorless. Color: Closest to 144A.

Flowering description:

*Flowering habit.*—'Balsundarco' is freely flowering under outdoor growing conditions with substantially continuous blooming from spring through autumn and year-round in greenhouse environment.

*Lastingness of individual flower on the plant.*—Approximately 9 to 12 days.

Flower description:

*General description.*—Type: Simple, salverform. Quantity per plant: Approximately 16. Fragrance: None.

*Bud.*—Rate of opening: Generally takes 1 to 2 days for bud to progress from first color to fully open flower. Quantity per plant: Approximately 5.

*Bud just before opening.*—Shape: Oblong. Length: Approximately 4.9 cm. Diameter at apex: Approximately 1.3 cm. Diameter at base: Approximately 4.6 mm. Texture: Densely glandular pubescent. Gland color: Colorless. Color of petals: Closest to 186C. Color of tube: Closest to 145D with venation of closest to 145C.

*Corolla.*—Diameter: Approximately 7.1 cm.

*Petals.*—Quantity: 5, fused to form a tube. Shape: Obovate. Appearance: Velvety. Margin: Entire, wavy. Apex: Acute. Length from tube: Approximately 3.5 cm. Length of free portion: Approximately 1.1 cm. Width: Approximately 3.5 cm. Texture of upper and lower surfaces: Glabrous. Color of upper surface when first open: 45B. Color of lower surfaces when first open. 186D. Color of upper surface when fully open: 50A. Color of lower surface when fully open: 50C fading to N155B at base with venation of 145B.

*Corolla tube.*—Length: Approximately 3.0 cm. Diameter at distal end: Approximately 1.2 cm. Diameter at proximal end: Approximately 3.0 mm. Texture of inner surface: Glabrous. Texture of outer surface: Densely pubescent. Color of inner surface: 160D with venation of 50A. Color of outer surface: Lighter than 144D with venation of 144D.

*Peduncle.*—Strength: Strong. Aspect: Acute angle to stem. Length: Approximately 3.1 cm. Diameter: Approximately 2.0 mm. Texture: Densely glandular pubescent with a mixture of long and short hairs. Gland color: Colorless. Color: 144A.

*Sepals.*—Quantity per flower: 5, fused at base. Shape: Linear. Apex: Acute. Length: Approximately 1.7 cm.

Width: Approximately 2.9 mm. Texture of upper and lower surfaces: Densely glandular pubescent with a mixture of long and short hairs. Gland color: Colorless. Color of upper and lower surfaces: 144A transitioning to 144B at base.

*Reproductive organs.*—Androecium: Stamen quantity: 5 per flower, partially fused to inside of corolla tube. Stamen length: Approximately 2.5 cm. Filament length of free portion: Approximately 1.6 cm. Filament color: 155C. Anther shape: Bilobed. Anther length: Approximately 1.0 mm. Anther color: 1D. Pollen amount: Abundant. Pollen color: 155A. Gynoecium: Pistil quantity: 1 per flower. Pistil length: Approximately 2.8 cm. Stigma shape: Funnel. Stigma length: Approximately 1.0 mm. Stigma color: 144A. Style length: Approximately 2.4 cm. Style color: 145D. Ovary diameter: Approximately 3.0 mm. Ovary color: 144A.

Seed and fruit production: Neither seed not fruit production has been observed.

Disease and pest resistance: Resistance to pathogens and pests common to *Petunia* has not been observed.

What is claimed is:

1. A new and distinct cultivar of *Petunia* plant named 'Balsundarco', substantially as herein shown and described.

* * * * *